United States Patent
Vernickel et al.

(10) Patent No.: US 8,812,078 B2
(45) Date of Patent: Aug. 19, 2014

(54) APPARATUS AND METHOD FOR DETERMINING AT LEAST ONE ELECTROMAGNETIC QUANTITY

(75) Inventors: Peter Vernickel, Hamburg (DE); Ulrich Katscher, Norderstedt (DE); Bernhard Gleich, Hamburg (DE); Jurgen Erwin Rahmer, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 294 days.

(21) Appl. No.: 13/388,108

(22) PCT Filed: Aug. 2, 2010

(86) PCT No.: PCT/IB2010/053497
§ 371 (c)(1),
(2), (4) Date: Jan. 31, 2012

(87) PCT Pub. No.: WO2011/015983
PCT Pub. Date: Feb. 10, 2011

(65) Prior Publication Data
US 2012/0126800 A1 May 24, 2012

(30) Foreign Application Priority Data
Aug. 7, 2009 (EP) .................... 09167496

(51) Int. Cl.
*A61B 5/05* (2006.01)
*G01V 3/00* (2006.01)

(52) U.S. Cl.
USPC ........................... 600/420; 324/300

(58) Field of Classification Search
USPC .............. 600/407, 409, 420, 410, 411, 422; 324/204, 228, 307, 318; 607/105; 73/53.01; 702/57
See application file for complete search history.

(56) References Cited

U.S. PATENT DOCUMENTS

| | | | |
|---|---|---|---|
| 2005/0052182 A1* | 3/2005 | Wollin | 324/307 |
| 2007/0241753 A1* | 10/2007 | Sodickson et al. | 324/307 |
| 2008/0204009 A1* | 8/2008 | Gleich et al. | 324/228 |

FOREIGN PATENT DOCUMENTS

DE 10151778 A1 8/2003
(Continued)

OTHER PUBLICATIONS
Gleich B et al. "Tomographic imaging using the nonlinear response of magnetic particles". 2005. Nature Publishing Group. Hamburg, Germany, vol. 435, pp. 1214-1217.

Primary Examiner — Long V. Le
Assistant Examiner — Lawrence Laryea (57) ABSTRACT

The present invention relates to an apparatus (100) for determining at least one electromagnetic quantity characterizing an electromagnetic property of an object, in particular a human body, wherein said object contains magnetic particles. The apparatus (100) applying the known principle of Magnetic Particle Imaging (MPI) comprises selection means for generating a magnetic selection field (50) having the known field pattern showing a field free point (FFP), drive means for changing the position in space of the FFP by means of a magnetic drive field, receiving means for acquiring detection signals depending on the magnetization of the magnetic particles within a field of view (28) and a reconstruction unit (152) for reconstructing a particle distribution quantity depending on the detection signals. The apparatus (100) further comprises a control unit (150) for controlling the receiving means for acquiring a first set of detection signals corresponding to a first drive field frequency and a second set of detection signals corresponding to a second drive field frequency, with both drive field frequencies differing from each other. The control unit (15) further controls the reconstruction unit (152) for reconstructing a first particle distribution quantity depending on the first set of detection signals and a second particle distribution quantity depending on the second set of detection signals. The apparatus (100) further comprises a determination unit (160) for determining the electromagnetic quantity depending on the first and second particle distribution quantity. The present invention further relates to a corresponding method as well as to a computer program.

15 Claims, 5 Drawing Sheets

(56) References Cited

FOREIGN PATENT DOCUMENTS

| | | |
|---|---|---|
| EP | 1304542 A2 | 4/2003 |
| WO | 2004091386 A2 | 10/2004 |
| WO | 2004091390 A2 | 10/2004 |
| WO | 2004091394 A2 | 10/2004 |
| WO | 2004091395 A2 | 10/2004 |
| WO | 2004091396 A2 | 10/2004 |
| WO | 2004091397 A2 | 10/2004 |
| WO | 2004091398 A2 | 10/2004 |
| WO | 2004091408 A2 | 10/2004 |
| WO | 2006064405 A1 | 6/2006 |
| WO | 2006122278 A2 | 11/2006 |
| WO | 2007017779 A2 | 2/2007 |
| WO | 2009074952 A2 | 6/2009 |

\* cited by examiner

APPARATUS AND METHOD FOR DETERMINING AT LEAST ONE ELECTROMAGNETIC QUANTITY

FIELD OF THE INVENTION

The present invention relates to an apparatus and a corresponding method for determining at least one electromagnetic quantity. Further, the present invention relates to a computer program for implementing said method on a computer and for controlling such an apparatus.

BACKGROUND OF THE INVENTION

In medical imaging, biological tissue properties are used to produce image contrasts. For example the electrical conductivity differs for different types of tissue. Therefore a conductivity quantity characterizing the conductivity distribution throughout at least a portion of a human body is significant for distinguishing different tissues of a human body. For instance, said conductivity quantity can be used to distinguish between tumours and healthy tissue or between necrotic and vital tissue after a myocardial infarction. Said conductivity quantity can also be used to support the characterization of brain tissue in connection with stroke or cerebral haemorrhage.

Numerous methods for determining electromagnetic quantities are known. For example a method called "Electric Impedance Tomography" (EIT) is used for conducting conductivity measurements and hence for determining a conductivity quantity. With this method numerous conducting electrodes are attached to the skin of a person to be examined and an electric current is applied across the electrodes. A great disadvantage of this method is the enormous amount of time needed for attaching the electrodes. There is also the fact that the spatial resolution is not very high.

In WO 2007/017779 A2 a method called "Electromagnetic Properties Tomography" (EPT) using a MRI system or MRI scanner is described. With this method an electrical permittivity distribution and/or an electrical conductivity distribution throughout a patient's body can be determined. With this method an excitation electro-magnetic field is applied to excite spins of an object. Magnetic resonance signals from the excited object are acquired. A magnetic induction field strength distribution is derived from the acquired magnetic resonance signals. Furthermore, an electric field strength distribution associated with the excitation electro-magnetic field is computed using the magnetic field and the Maxwell equations. The electrical permittivity distribution and/or the electrical conductivity distribution are computed from the electric field strength distribution and the magnetic induction field strength distribution. Although the amount of time needed for doing preparations before a measurement can be conducted is comparatively small, the use of this method is restricted because of the following disadvantages: Firstly, the frequency of the excitation electro-magnetic field is fixed to the so-called Larmor frequency of the MR system involved, with this frequency being significantly higher than the frequencies required for the majority of corresponding investigations. Secondly, as it is impossible to rotate the excitation electro-magnetic field with a MR system, an anisotropy of the electric conductivity can be investigated only for very few, partially "rotatable" body parts like hands, feet, and head. Thirdly, a MR scanner is a rather expensive imaging modality, particularly since for EPT it is "just" used to generate and measure magnetic fields.

"Magnetic Particle Imaging" (MPI) is an emerging medical imaging modality. The first versions of MPI were two-dimensional in that they produced two-dimensional images. Future versions will be three-dimensional (3D). A time-dependent, or 4D, image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, a MP image of an object's volume of interest is generated in two steps. The first step, referred to as data acquisition, is performed using a MPI scanner. The MPI scanner has means to generate a static magnetic gradient field, called "selection field", which has a single field free point (FFP) at the isocenter of the scanner. In addition, the scanner has means to generate a time-dependent, spatially nearly homogeneous magnetic field. Actually, this field is obtained by superimposing a rapidly changing field with a small amplitude, called "drive field", and a slowly varying field with a large amplitude, called "focus field". By adding the time-dependent drive and focus fields to the static selection field, the FFP may be moved along a predetermined FFP trajectory throughout a volume of scanning surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles; if the object is an animal or a patient, a contrast agent containing such particles is administered to the animal or patient prior to the scan. During the data acquisition, the MPI scanner steers the FFP along a deliberately chosen trajectory that traces out the volume of scanning, or at least the field of view. The magnetic nanoparticles within the object experience a changing magnetic field and respond by changing their magnetization. The changing magnetization of the nanoparticles induces a time dependent voltage in each of the receive coils. This voltage is sampled in a receiver associated with the receive coil. The samples output by the receivers are recorded and constitute the acquired data. The parameters that control the details of the data acquisition make up the scan protocol.

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model is an integral operator that acts on the acquired data; the reconstruction algorithm tries to undo, to the extent possible, the action of the model.

Such an MPI apparatus and method have the advantage that they can be used to examine arbitrary examination objects—e.g. human bodies—in a non-destructive manner and without causing any damage and with a high spatial resolution, both close to the surface and remote from the surface of the examination object. Such an arrangement and method are generally known and are first described in DE 101 51 778 A1 and in Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication take advantage of the non-linear magnetization curve of small magnetic particles. As yet MPI apparatuses and methods are not adapted for determining electromagnetic quantities.

SUMMARY OF THE INVENTION

It is an object of the present invention to provide an alternative apparatus and corresponding method for determining at least one electromagnetic quantity characterizing an electromagnetic property of an object, in particular a human body, as well as a computer program, by which measurements can be conducted at arbitrary frequencies, in particular low frequencies, and by which the direction of the magnetic field can be rotated.

In a first aspect of the present invention an apparatus for determining at least one electromagnetic quantity characterizing an electromagnetic property of an object, in particular a human body, wherein said object contains magnetic particles, is presented comprising:

selection means comprising a selection field signal generator unit and selection field elements for generating a magnetic selection field having a pattern in space of its magnetic field strength such that a first sub-zone having a low magnetic field strength and a second sub-zone having a higher magnetic field strength are formed in a field of view, drive means comprising a drive field signal generator unit and drive field coils for changing the position in space of the two sub-zones in the field of view by means of a magnetic drive field so that the magnetization of the magnetic particles contained in said object changes locally, receiving means comprising at least one signal receiving unit and at least one receiving coil for acquiring detection signals, which detection signals depend on the magnetization in the field of view, which magnetization is influenced by the change in the position in space of the first and second sub-zone, a reconstruction unit for reconstructing a particle distribution quantity characterizing a spatial distribution of the magnetic particles within at least a portion of the object depending on the detection signals, a control unit for controlling the receiving unit for acquiring a first set of detection signals corresponding to a first drive field frequency and for acquiring a second set of detection signals corresponding to a second drive field frequency, wherein the first and the second drive field frequency differ from each other, and for controlling the reconstruction unit for reconstructing a first particle distribution quantity depending on the first set of detection signals and for reconstructing a second particle distribution quantity depending on the second set of detection signals, wherein the reconstruction unit contains a determination unit for determining the electromagnetic quantity depending on the first and the second particle distribution quantity.

In a further aspect of the present invention a method for determining at least one electromagnetic quantity characterizing an electromagnetic property of an object, in particular a human body, wherein said object contains magnetic particles, is presented comprising the steps of:

generating a magnetic selection field having a pattern in space of its magnetic field strength such that a first sub-zone having a low magnetic field strength and a second sub-zone having a higher magnetic field strength are formed in a field of view, changing the position in space of the two sub-zones in the field of view by means of a magnetic drive field so that the magnetization of the magnetic particles contained in said object changes locally, acquiring detection signals, which detection signals depend on the magnetization in the field of view, which magnetization is influenced by the change in the position in space of the first and second sub-zone, reconstructing a particle distribution quantity characterizing a spatial distribution of the magnetic particles within at least a portion of the object depending on the detection signals, controlling the acquiring of a first set of detection signals corresponding to a first drive field frequency and the acquiring of a second set of detection signals corresponding to a second drive field frequency, wherein the first and the second drive field frequency differ from each other, controlling the reconstructing of a first particle distribution quantity depending on the first set of detection signals and the reconstructing of a second particle distribution quantity depending on the second set of detection signals, and determining the electromagnetic quantity depending on the first and the second particle distribution quantity In a still further aspect of the present invention a corresponding computer program is presented comprising program code means for causing a computer to control an said apparatus to carry out the steps of said method when said computer program is carried out on the computer.

Preferred embodiments of the invention are defined in the dependent claims. It shall be understood that the claimed method and the claimed computer program have similar and/or identical preferred embodiments as the claimed apparatus and as defined in the dependent claims.

The present invention is principally based on the idea of using a Magnetic Particle Imaging (MPI) system and therefore a MPI scanner for generating and determining magnetic fields inside a volume of interest, in particular inside at least a portion of a human body or a patient. For conducting measurements using a MPI system the object to be examined must contain magnetic particles. The obtained spatially resolved magnetic fields are used for determining at least one electromagnetic quantity (e.g. using Maxwell equations), wherein the electromagnetic quantity characterizes an electromagnetic property of the object. Thus, reconstructing a patient's electric properties and in turn distinguishing between different tissues of a human body is possible. Using a MPI scanner allows generating magnetic fields showing a very wide frequency range at least compared to MRI. In particular it is possible to generate magnetic fields showing low frequencies, which are clearly lower than the frequency typically applied in MRI, wherein MRI frequencies are typically higher than 40 MHz (f>40 MHz). Thus, for example investigating the frequency spectrum of an electromagnetic quantity is possible. Furthermore, the direction of the magnetic field generated with a MPI scanner can be easily rotated. This allows for example investigations of the anisotropy of an electromagnetic quantity. Last but not least, with regard to the acquisition costs a MPI scanner is significantly cheaper than a MRI scanner.

The concrete approach using a MPI system or MPI scanner is as follows: acquiring a first set of detection signals corresponding to a first drive field frequency and acquiring a second set of detection signals corresponding to a second drive field frequency, wherein the first and the second drive field frequency differ from each other. Depending on the first set of detection signals a first particle distribution quantity and depending on the second set of detection signals a second particle distribution quantity are reconstructed. Finally, the electromagnetic quantity is determined depending on the first and the second particle distribution quantity.

For the following reason two sets of detection signals corresponding to two different drive field frequencies are determined: the interaction between the magnetic field or RF field generated by the coils of the MPI system and the object to be examined or imaged gets more pronounced with increasing drive field frequencies. Said interaction is a precondition for determining electromagnetic quantities or for conducting Electromagnetic Properties Tomography. Said interaction comprises induced currents, losses and attenuation, which distort the magnetic field generated by the MPI scanner. This distortion has an impact on the set of detection signals and therefore inevitably on the particle distribution quantity reconstructed depending on the set of detection signals. Hence, the particle distribution quantity does not solely represent the distribution of the magnetic particles or the contrast agent contained in the object to be examined but it is also influenced by said field distortion effects.

For quantifying the field distortion effects and therefore for extracting the amount of the set of detection signals arising from the field distortion and consequently for extracting the amount of the particle distribution quantity arising from the field distortion two MPI measurements with two different magnetic drive fields showing different drive field frequencies are performed. A first measurement is performed, choosing a first trajectory and therefore a first drive field frequency to generate a first signal spectrum with predominantly low frequency components. Because of the low drive field frequency the first set of detection signals acquired with this first measurement and therefore the first particle distribution quantity represent for the most part solely the distribution of the magnetic particles, as it is given by the anatomy of the body to be examined and therefore the different types of tissues contained in said body. A second measurement is performed, choosing a second trajectory and therefore a second drive field frequency to generate a second signal spectrum with predominantly high frequency components. Because of the high drive field frequency the second set of detection signals acquired with this second measurement and therefore the second particle distribution quantity also represent the distribution of the magnetic particles but blurred by the above described field distortion effects. The second drive field frequency has to be high enough for stimulating the body to be examined such that the field distortion effects occur distinctly.

As for determining the electromagnetic quantity two particle distribution quantities are used, the amount of the second particle distribution quantity representing the field distortion effects needed for determining the electromagnetic quantity can be extracted by eliminating the amount of the second particle distribution quantity representing the distribution of the magnetic particles. Therefore, determining of an electromagnetic quantity in a very easy way, without the need of having detailed information about the concrete anatomy of the body to be examined is possible.

It turned out that the first drive field frequency lies advantageously within a first frequency range that is below a maximum frequency of 100 kHz ($f_1 < 100$ kHz) and that the second drive field frequency lies advantageously within a second frequency range having a lowest frequency being higher than 1 MHz and a highest frequency being lower than roughly 10 MHz (1 MHz $< f_2 <$ 10 MHz).

According to a preferred embodiment the control unit is adapted for controlling the drive field signal generator unit for generating a first magnetic drive field showing the first drive field frequency and for generating a second magnetic drive field showing the second drive field frequency. This measure allows a precise selection of both drive field frequencies and thus a best possible extraction of the amount of the second particle distribution quantity representing the field distortion effects. Hence, the best result in determining the electromagnetic quantity is received.

Advantageously a drive field amplitude is selected in addition to the drive field frequency. It turned out that the best results in determining the electromagnetic quantity are obtained in case the first magnetic drive field has a small first drive field amplitude and the second magnetic drive field has a large drive field amplitude. That means the first drive field amplitude is smaller than the second drive amplitude ($A_1 < A_2$).

According to a further embodiment the control unit is adapted for controlling the drive field signal generator unit so that the first and the second magnetic drive field are generated successively. This measure has the advantage that both sets of detection signals are acquired separately and therefore the amount of the second particle distribution quantity representing the field distortion effects needed for determining the electromagnetic quantity can be extracted at best resulting in a very precise determination of the electromagnetic quantity.

According to another embodiment, the control unit is adapted for controlling the drive field signal generator unit for generating a third magnetic drive field showing simultaneously the first and the second drive field frequency. With this measure the time required for determining the electromagnetic quantity is reduced, as only one single measurement with one single magnetic drive field is conducted instead of two separate measurements with two separate magnetic drive fields. In a first embodiment the third magnetic drive field arises from superimposing the first and the second magnetic drive field. This is achieved by generating a drive field current flowing through the drive field coils that is a superimposition of a first drive field current flowing through the drive field coils in case solely the first magnetic drive field is generated and a second drive field current flowing through the drive field coils in case solely the second magnetic drive field is generated. In a second embodiment a drive field current is used containing the first drive field frequency as a fundamental oscillation and several harmonics, wherein one of the harmonics is the second drive field frequency.

Further, in case the third magnetic drive field arises from superimposing a first and a second magnetic drive field it is thinkable that the first magnetic drive field has a first dominating field component and therefore a first direction allowing measurement in this direction and that the second magnetic drive field has s second dominating field component and therefore a second direction allowing measurement in this direction.

According to another embodiment, the determination unit is adapted for determining the electromagnetic quantity depending on a quotient formed with the first and the second particle distribution quantity. This is an easy, not very time-consuming measure for reliably extracting the amount of the second particle distribution quantity representing the field distortion effects needed for determining the electromagnetic quantity.

In a preferred embodiment the two sub-zones take up first positions in space along a first trajectory corresponding to the first drive field frequency and second positions in space along a second trajectory corresponding to the second drive field frequency, wherein the control unit is adapted for controlling the drive field signal generator unit so that the first positions and the second positions substantially correspond to each other. The advantage of this measure is that influences arising from different positions in space the two sub-zones and therefore the field free point could take up conducting the first and the second measurement are eliminated. Hence, a very precise determination of the electromagnetic quantity is possible.

According to a further embodiment, the determination unit is adapted for determining an actual magnetic field strength quantity depending on the first and the second particle distribution quantity for determining the electromagnetic quantity. This measure represents a very easy approach for determining an electromagnetic quantity rapidly and reliably. The particle distribution quantity characterizes the spatial distribution of the magnetic particles within at least a portion of the object to be examined. Therefore, with using said particle distribution quantity an actual magnetic field strength quantity representing a magnetic field to which the portion of the body is exposed can be determined very precisely. Said actual magnetic field strength quantity can be used as a quantity for easily and reliably determining an electromagnetic quantity or for determining an intermediate quantity that in turn is the basis for determining an electromagnetic quantity, as for such a determination Maxwell equations can be applied. Advantageously the actual magnetic field strength quantity represents the magnetic field resulting from a superimposition of the magnetic selection field and the magnetic drive field showing the second drive field frequency. Said resulting magnetic field is also referred to as applied magnetic field. If present, a further field component exists, resulting from a magnetic focus field. The shape of the resulting magnetic field corresponds to the shape usually occurring at a standard MPI measurement.

According to another embodiment, the determination unit is adapted for determining the actual magnetic field strength quantity depending on a reference magnetic field strength quantity. With this measure the actual magnetic field strength can be determined in a very easy and reliable manner, as no detailed information about the geometry and the electric properties of the object to be examined is needed. Advantageously the reference magnetic field strength quantity describes the magnetic field resulting from superimposition of the magnetic selection field and the magnetic drive field showing the first drive field frequency. As considering the magnetic drive field showing the first drive field frequency, the reference magnetic field strength quantity can be easily derived from the geometry of the drive field coils and from the selection field coils using Biot-Savarts law.

According to a further embodiment, the control unit is adapted for controlling the drive field signal generator unit for varying the direction of the magnetic drive field. This measure allows investigations with regard to the anisotropic behavior of biological tissues and thus electromagnetic quantity anisotropy investigations. As already mentioned, the conductivity quantity characterizing a conductivity distribution throughout a human body is of great relevance in the area of medical imaging. With said conductivity even knowledge about its anisotropy is of interest. The conductivity anisotropy of a biological tissue might play a diagnostic role, for example for identifying structural damage of cardiac muscle fiber or neural fibers in the brain. For conducting electromagnetic quantity anisotropy investigations the direction of the first magnetic drive field showing the first drive field frequency has to be varied as well as the direction of the second magnetic drive field showing the second drive field frequency. Advantageously both directions are varied in essentially equal measure.

According to another embodiment, the apparatus further comprises a storage unit for storing a set of system data of the apparatus' system function. The set of system data is acquired by conducting a calibration measurement timely before the real measurements are conducted for determining for example an electromagnetic quantity. It is also thinkable to conduct the calibration measurement timely after the real measurements were conducted. With said calibration measurement a so called system function is determined. Said system function establishes the relation between the spatial position of the magnetic particles contained in an object to be examined and frequency response and therefore the detection signals acquired with the receiving means. The system function describes inherently the properties of the MPI scanner, in particular fields generated by the unloaded coils, and the properties of the contrast agent used. A calibration measurement has to be done once for a setup of coils and a contrast agent.

According to a further embodiment, the determination unit is adapted for determining an electric field strength quantity. Said electric field quantity characterizes an electric field related to the magnetic field characterized by the actual magnetic field strength quantity. This measure allows determination of electromagnetic quantities that can not directly be determined depending on a magnetic field strength quantity. Thus, a comprehensive determination of different electromagnetic quantities is possible.

According to another embodiment, as electromagnetic quantity at least one of a conductivity quantity characterizing a conductivity distribution throughout the portion of the object, a permittivity quantity characterizing a permittivity distribution throughout the portion of the object and a specific absorption rate quantity characterizing a local specific energy absorption rate throughout the portion of the object is determined. As a whole, diverse electromagnetic quantities are available, enabling an extensive distinction of various biological tissues. Among the electromagnetic quantities listed above, the conductivity quantity might be of greatest relevance, as many tissue distinctions are based on this quantity. Electric conductivity imaging might result in a new modality of medical imaging with numerous applications. Further, the conductivity quantity is used for determining other electromagnetic quantities, fore example said specific absorption rat quantity. In the context of the explanations above and below, the specific absorption rate (SAR) quantity is also considered as an electromagnetic quantity characterizing an electromagnetic property of an object, as said quantity characterizes the rate at which energy is absorbed by a biological tissue when exposed to a radio frequency or electromagnetic field.

According to a further embodiment, the reconstruction unit is adapted for transmitting the electromagnetic quantity to a computer for displaying the spatial distribution of the electromagnetic quantity throughout the portion of the object on a monitor. Displaying the spatial distribution of the electromagnetic quantity on a monitor has the advantage of easily getting an overview at which parts of the examined object abnormalities in the biological tissue exists. In addition, this measure allows an immediate evaluation of the result obtained with a first measurement and conducting subsequently a refined second measurement if necessary.

As already explained, the object to be examined using a MPI system must contain magnetic particles. If the object is an animal or a patient, said magnetic particles get into the object or body by administering a contrast agent containing such magnetic particles. Hence a distribution of magnetic particles within a body can also be considered as a distribution of the contrast agent.

The terms conductivity and permittivity used in the explanations above and below stand for the terms electrical conductivity and electrical permittivity.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 4. In particular, two embodiments of an MPI scanner for medical diagnostics will be described. An informal description of the data acquisition is also given. The similarities and differences between the two embodiments will be pointed out.

Figure 1:
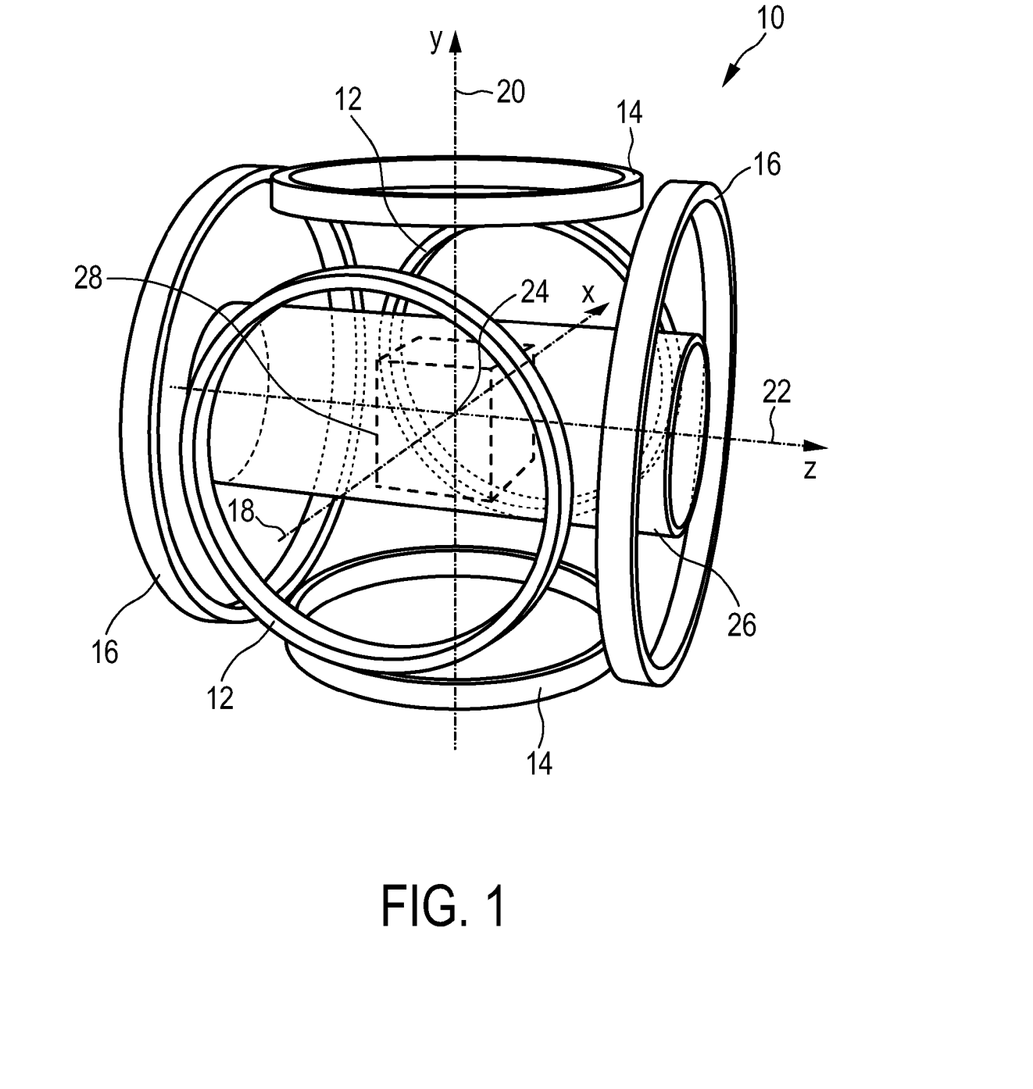
FIG. 1 shows a first embodiment of an MPI apparatus.

The first embodiment 10 of an MPI scanner shown in FIG. 1 has three prominent pairs 12, 14, 16 of coaxial parallel circular coils, each pair being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x and z-axes are horizontal. The coil pairs 12, 14, 16 are also named after their axes. For example, the y-coil pair 14 is formed by the coils at the top and the bottom of the scanner. Moreover, the coil with the positive (negative) y-coordinate is called the $y^+$-coil ($y^-$-coil), and similarly for the remaining coils.

The scanner 10 can be set to direct a predetermined, time dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the $z^+$-coil, and the current —$I^S$ is made to flow through the $z^-$-coil. The z-coil pair 16 then acts as an anti-parallel circular coil pair.

Figure 2:
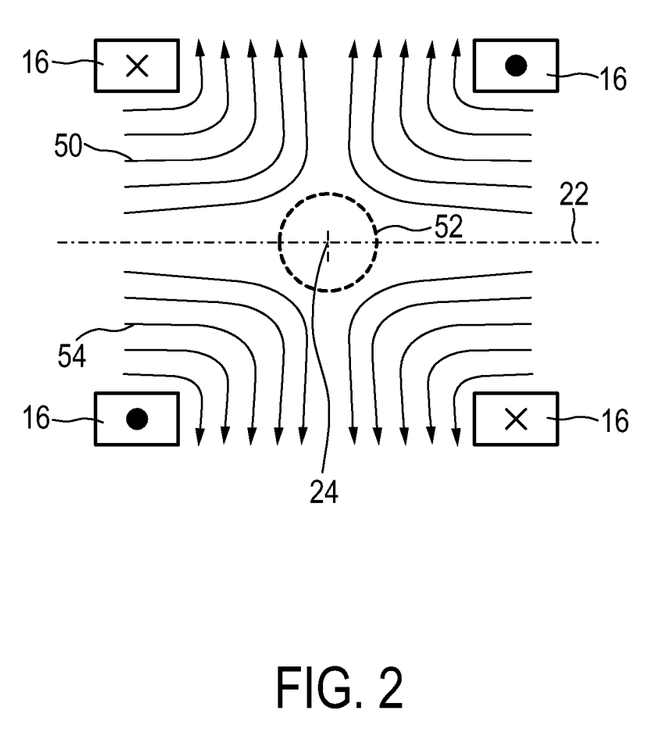
FIG. 2 shows an example of the selection field pattern produced by an apparatus as shown in FIG. 1.

The magnetic selection field which is generally a gradient magnetic field is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field characterized by the field lines 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. The first sub-zone 52 of the scanner's field of view 28 is preferably a spatially coherent area. The same applies to the field-free point contained in the first sub-zone 52. The first sub-zone 52 may also be a punctiform area, a line or a flat area. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 within the field of view 28 the (overall) magnetization in the field of view 28 changes. By measuring the magnetization in the field of view 28 or physical parameters influenced by the magnetization, information about the spatial distribution of the magnetic particles in the field of view 28 can be obtained. In order to change the relative spatial position of the two sub-zones 52, 54 in the field of view 28, further magnetic fields, i.e. the magnetic drive field, and, if applicable, the magnetic focus field, are superimposed to the selection field characterized by the field lines 50 in the field of view 28 or at least in a part of the field of view 28.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field. The current flowing through the $z^\pm$-coil is $I^D_3+I^F_3+I^S$. The current flowing through the remaining two coil pairs 12, 14 is $I^D_k+I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time dependent. The difference between the focus field and the drive field is that the focus field varies slowly in time and has a large amplitude while the drive field varies rapidly and has a small amplitude. There are physical and biomedical reasons to treat these fields differently. A rapidly varying field with a large amplitude would be difficult to generate and hazardous to the patient.

The MPI scanner 10 has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair. The receive coils are supposed to be well decoupled. The time dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from DC up to the point where the expected signal level drops below the noise level.

The MPI scanner 10 shown in FIG. 1 has a cylindrical bore 26 along the z-axis 22, i.e. along the axis of the selection field. All coils are placed outside this bore 26. For the data acquisition, the patient (or object) to be imaged (or treated) is placed in the bore 26 such that the patient's volume of interest—that volume of the patient (or object) that shall be imaged (or treated)—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, or a cylinder. A cubical field of view 28 is illustrated in FIG. 1.

The size of the first sub-zone 52 is dependent on the one hand on the strength of the gradient of the magnetic selection field and on the other hand on the field strength of the magnetic field required for saturation. For a sufficient saturation of the magnetic particles at a magnetic field strength of 80 A/m and a gradient (in a given space direction) of the field strength of the magnetic selection field amounting to $50 \times 10^3$ A/m$^2$, the first sub-zone 52 in which the magnetization of the particles is not saturated has dimensions of about 1 mm (in the given space direction).

The patient's volume of interest is supposed to contain magnetic nanoparticles. Especially prior to a therapeutic and/or diagnostic treatment of, for example, a tumor, the magnetic particles are positioned in the volume of interest, e.g. by means of a liquid comprising the magnetic particles which is injected into the body of the patient (object) or otherwise administered, e.g. orally, to the patient. The liquid comprising the magnetic particles is called contrast agent.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 μm, a magnetic field of approximately 800 A/m (corresponding approximately to a flux density of 1 mT) is then required, whereas in the case of a diameter of 100 μm a magnetic field of 80 A/m suffices. Even smaller values are obtained when a coating of a material having a lower saturation magnetization is chosen or when the thickness of the layer is reduced. Magnetic particles that can generally be used are available on the market under the trade name Resovist.

For further details of the generally usable magnetic particles and particle compositions, the corresponding parts of EP 1304542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

The data acquisition starts at time $t_s$ and ends at time $t_e$. During the data acquisition, the x-, y-, and z-coil pairs 12, 14, 16 generate a position- and time dependent magnetic field, the applied field. This is achieved by directing suitable currents through the coils. In effect, the drive and focus fields push the selection field around such that the FFP moves along a preselected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time dependent voltage $V_k$ across the terminals of receive coil pair along the $x_k$-axis. The associated receiver converts this voltage to a signal $S_k(t)$, which it samples and outputs.

It is advantageous to receive or to detect signals from the magnetic particles located in the first sub-zone 52 in another frequency band (shifted to higher frequencies) than the frequency band of the magnetic drive field variations. This is possible because frequency components of higher harmonics of the magnetic drive field frequency occur due to a change in magnetization of the magnetic particles in the scanner's field of view 28 as a result of the non-linearity of the magnetization characteristics.

Figure 3:
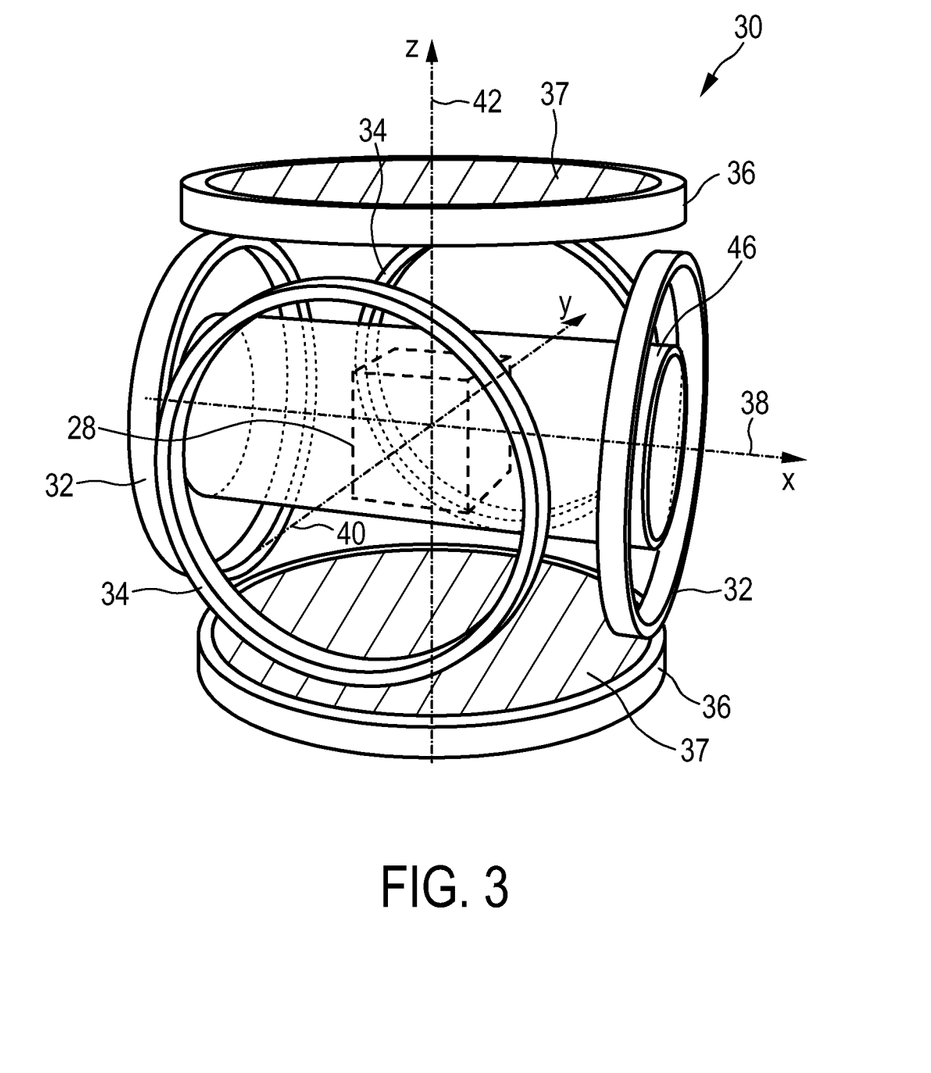
FIG. 3 shows a second embodiment of an MPI apparatus.

FIG. 3 shows a second embodiment of a MP scanner 30. Like the first embodiment shown in FIG. 1, the second embodiment of the MPI scanner 30 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The bore 46 contains a field of view 28. The drive field is generated by a solenoid (not shown) along the x-axis 38 and by pairs of saddle coils (not shown) along the two remaining axes 40, 42. These coils are wound around a tube which forms the bore. The drive field coils also serve as receive coils. The signals picked up by the receive coils are sent through a high-pass filter that suppresses the contribution caused by the applied field.

To give a few typical parameters of such an embodiment: The z-gradient of the selection field, G, has a strength of $G/\mu_0 = 2.5$ T/m, where $\mu_0$ is the vacuum permeability. The selection field generated does either not vary at all over the time or the variation is comparably slow, preferably between approximately 1 Hz and approximately 100 Hz. The temporal frequency spectrum of the drive field is concentrated in a narrow band around 25 kHz (up to approximately 100 kHz). The useful frequency spectrum of the received signals lies between 50 kHz and 1 MHz (eventually up to approximately 10 MHz). The bore has a diameter of 120 mm. The biggest cube that fits into the bore 46 has an edge length of 120 mm/$\sqrt{2} \approx 84$ mm.

As shown in the above embodiments the various magnetic fields can be generated by coils of the same coils pairs and by providing these coils with appropriately generated currents. However, and especially for the purpose of a signal interpretation with a higher signal to noise ratio, it may be advantageous when the temporally constant (or quasi constant) selection field and the temporally variable drive field and focus field are generated by separate coil pairs. Generally, coil pairs of the Helmholtz type can be used for these coils, which are generally known, e.g. from the field of magnetic resonance apparatus with open magnets (open MRI) in which a radio frequency (RF) coil pair is situated above and below the region of interest, said RF coil pair being capable of generating a temporally variable magnetic field. Therefore, the construction of such coils need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

Figure 4:
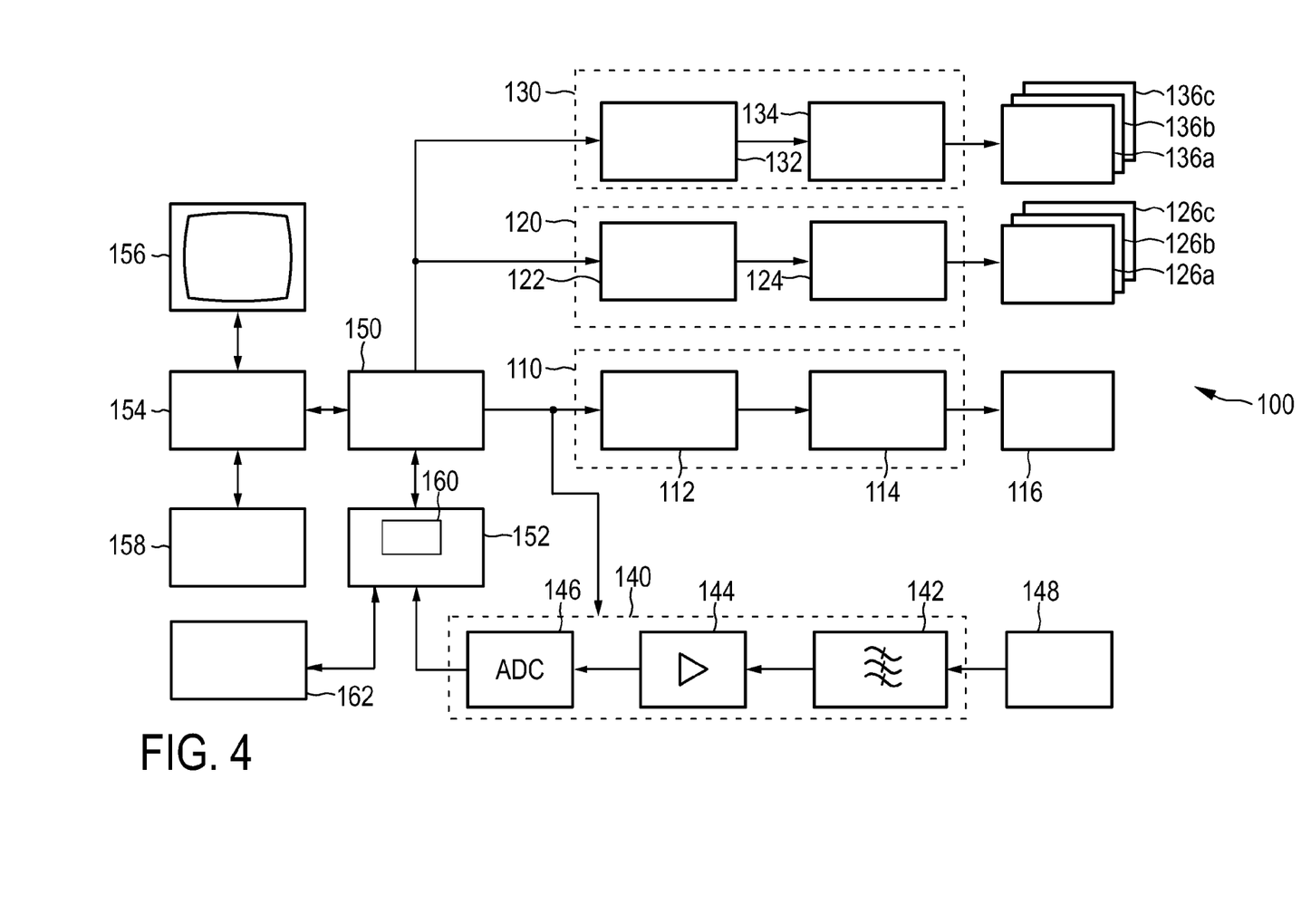
FIG. 4 shows a block diagram of an MPI apparatus according to the present invention.

FIG. 4 shows a general block diagram of an MPI apparatus 100 according to the present invention. With the apparatus 100 at least one electromagnetic quantity can be determined. Said electromagnetic quantity characterizes an electromagnetic property of an object containing magnetic particles. Said object might be a human or a animal body. In case of a body the electromagnetic quantity characterizes an electromagnetic property of biological tissue contained in said body. The general principles of magnetic particle imaging and of magnetic resonance imaging explained above are valid and applicable to this embodiment as well, unless otherwise specified.

The embodiment of the apparatus 100 shown in FIG. 4 comprises a set of various coils for generating the desired magnetic fields. First, the coils and their functions in a MPI mode shall be explained.

For generating the magnetic (gradient) selection field explained above, selection means are provided comprising a set of selection field (SF) coils 116, preferably comprising at least one pair of coil elements. The selection means further comprises a selection field signal generator unit 110. Preferably, a separate generator subunit is provided for each coil element (or each pair of coil elements) of the set 116 of selection field coils. Said selection field signal generator unit 110 comprises a controllable selection field current source 112 (generally including an amplifier) and a filter unit 114 which provide the respective section field coil element with the selection field current to individually set the gradient strength of the selection field in the desired direction. Preferably, a DC current is provided. If the selection field coil elements are arranged as opposed coils, e.g. on opposite sides of the field of view, the selection field currents of opposed coils are preferably oppositely oriented. With said selection means a magnetic selection field having a pattern in space of its magnetic field strength such that a first sub-zone 52 having a low magnetic field strength and a second sub-zone 54 having a higher magnetic field strength are formed in a field of view 28, as it shown in FIG. 2.

The selection field signal generator unit 110 is controlled by a control unit 150, which preferably controls the selection field current generation 110 such that the sum of the field strength and the sum of the gradient strength of all spatial fractions of the selection field is maintained at a predefined level.

For generation of a magnetic focus field the apparatus 100 further comprises focus means comprising a set of focus field (FF) coils, preferably comprising three pairs 126a, 126b, 126c of oppositely arranged focus field coil elements. Said magnetic focus field is generally used for changing the position in space of the region of action. The focus field coils are controlled by a focus field signal generator unit 120, preferably comprising a separate focus field signal generation subunit for each coil element (or at least each pair of coil elements) of said set of focus field coils. Said focus field signal generator unit 120 comprises a focus field current source 122 (preferably comprising a current amplifier) and a filter unit 124 for providing a focus field current to the respective coil of said subset of coils 126a, 126b, 126c which shall be used for generating the magnetic focus field. The focus field current unit 120 is also controlled by the control unit 150.

For generation of the magnetic drive field the apparatus 100 further comprises drive means comprising a subset of drive field (DF) coils, preferably comprising three pairs 136a, 136b, 136c of oppositely arranged drive field coil elements. The drive field coils are controlled by a drive field signal generator unit 130, preferably comprising a separate drive field signal generation subunit for each coil element (or at least each pair of coil elements) of said set of drive field coils. Said drive field signal generator unit 130 comprises a drive field current source 132 (preferably including a current amplifier) and a filter unit 134 for providing a drive field current to the respective drive field coil. The drive field current source 132 is adapted for generating an AC current and is also controlled by the control unit 150. With said drive means the position in space of the two sub-zones 52, 54 in the field of view 28 can be changed by means of a magnetic drive field so that the magnetization of the magnetic particles contained in said object changes locally.

For signal detection the apparatus 100 further comprises receiving means comprising a receiving coil 148 and a signal receiving unit 140, which receives signals detected by said receiving coil 148. Said signal receiving unit 140 comprises a filter unit 142 for filtering the received detection signals. The aim of this filtering is to separate measured values, which are caused by the magnetization in the examination area which is influenced by the change in position of the two part-regions 52, 54, from other, interfering signals. To this end, the filter unit 142 may be designed for example such that signals which have temporal frequencies that are smaller than the temporal frequencies with which the receiving coil 148 is operated, or smaller than twice these temporal frequencies, do not pass the filter unit 142. The signals are then transmitted via an amplifier unit 144 to an analog/digital converter 146 (ADC). The digitalized signals produced by the analog/digital converter 146 are fed to a reconstruction unit 152 (also called image processing unit). Thus, with the receiving means detection signals are acquired. Said detection signals depend on the magnetization in the field of view 28, which magnetization is influenced by the change in the position in space of the first and second sub-zone 52, 54, Said detection signals are forwarded in a digitized form to the reconstruction unit.

The reconstruction unit reconstructs the spatial distribution of the magnetic particles from the detection signals received from the receiving unit and from the respective position which the first part-region 52 takes up in the examination area at that time at which the detection signal to be processed was acquired with the receiving means. The reconstruction unit 152 obtains the position from the control unit 150. The reconstructed spatial distribution of the magnetic particles is finally transmitted via the control unit 150 to a computer 154, which displays it on a monitor 156. Thus, an image can be displayed showing the distribution of magnetic particles in the field of view of the examination area. Thus, with the reconstruction unit 152 a particle distribution quantity characterizing the spatial distribution of the magnetic particles within at least a portion of the object to be examined is determined depending on the detection signals. The particle distribution quantity is forwarded to the computer 154 via the control unit 150.

Further, an input unit 158 is provided, for example a keyboard. A user is therefore able to set the desired direction of the highest resolution and in turn receives the respective image of the region of action on the monitor 156. If the critical direction, in which the highest resolution is needed, deviates from the direction set first by the user, the user can still vary the direction manually in order to produce a further image with an improved imaging resolution. This resolution improvement process can also be operated automatically by the control unit 150 and the computer 154. The control unit 150 in this embodiment sets the gradient field in a first direction which is automatically estimated or set as start value by the user. The direction of the gradient field is then varied stepwise until the resolution of the thereby received images, which are compared by the computer 154, is maximal, respectively not improved anymore. The most critical direction can therefore be found respectively adapted automatically in order to receive the highest possible resolution.

In the following the components contained in and the aspects of the MPI apparatus 100 according to the invention are described.

The apparatus further comprises a storage unit 162 for storing a set of system data of the apparatus' system function. The set of system data is acquired by conducting a calibration measurement timely before the real measurements are conducted for determining the electromagnetic quantity. The reconstruction unit 152 contains a determination unit 160 for determining the electromagnetic quantity.

According to the invention the control unit 150 is adapted for controlling the receiving unit for acquiring a first set of detection signals corresponding to a first drive field frequency and for acquiring a second set of detection signals corresponding to a second drive field frequency, wherein the first and the second drive field frequency differ from each other. Controlling the receiving unit 140 means for example adjusting the frequency characteristic of the filter unit 142 and/or adjusting the amplification characteristic of the amplifier unit 144 and/or adjusting the sampling characteristic of the analog/digital converter 146 to the detection mode.

Further the control unit 150 is adapted for controlling the reconstruction unit 152 for reconstructing a first particle distribution quantity depending on the first set of detection signals and for reconstructing a second particle distribution quantity depending on the second set of detection signals. Both particle distribution quantities are forwarded to the determination unit 160 contained in the reconstruction unit. The determination unit 160 determines the electromagnetic quantity depending on the first and the second particle distribution quantity. The reconstruction unit 152 in turn is adapted for transmitting the electromagnetic quantity via the control unit 150 to the computer 154 for displaying the spatial distribution of the electromagnetic quantity throughout the portion of the examined object on the monitor 156.

On the computer 154 a computer program is carried out, wherein said computer program comprises program code means for causing the computer 154 to control the apparatus 100 to carry out the steps of the method according to the invention.

Figure 5:
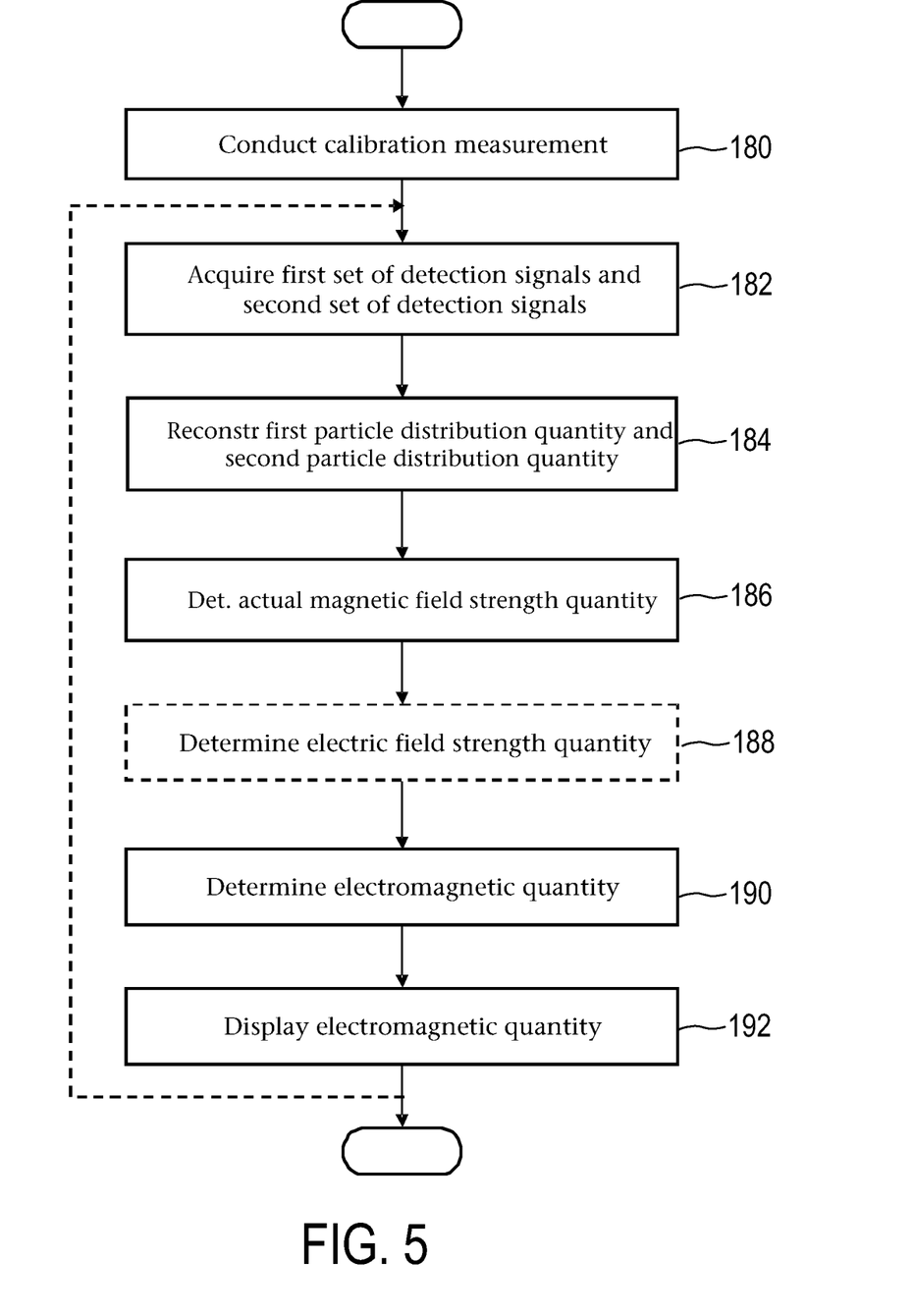
FIG. 5 shows a flow chart of an MPI method according to the present invention.

FIG. 5 shows a flowchart of an embodiment of the method according to the present invention. With the following explanations it is assumed that the magnetic drive field has a dominant component being orientated in x-direction. This shall not have any restricting impact on the invention. Of course, the magnetic drive field may also have a dominant component being orientated in y-direction or z-direction.

In a step 180 a calibration measurement is conducted. With said calibration measurement a so called system function is determined. The corresponding set of system data is stored in the storage unit 162. The calibration measurement is conducted timely before real measurements for determining an electromagnetic quantity are conducted. With the real measurement a MPI sequence is used for imaging the object of interest. Said object of interest is for example at least a portion of a human or animal body, in particular tissue contained in such a body. The system function is used to reconstruct an image from the measured data, wherein the image shows the distribution of the contrast agent within vital tissue.

The procedure of a real measurement starts at step 182. In step 182 a first set of detection signals corresponding to a first drive field frequency and a second set of detection signals corresponding to a second drive field frequency are acquired. Both drive field frequencies differ from each other. For this purpose the control unit 150 controls the drive field signal generator unit 130 for generating a first magnetic drive field showing the first drive field frequency and for generating a second magnetic drive field showing the second drive field frequency. In doing so, several approaches are thinkable. In a first approach the control unit 150 controls the drive field signal generator unit 130 so that the first and the second magnetic drive field are generated successively. Whereas in a second approach the control unit 150 controls the drive field signal generator unit 130 for generating a third magnetic drive field showing simultaneously the first and the second drive field frequency.

As already mentioned, the FFP is moved along a certain trajectory over the field of view. For this purpose a sequence of varying currents has to flow in the drive field coils 136a, 136b, 136c. Advantageously a special class of trajectories, the Lissajous trajectories is chosen. For example a Lissajous trajectory with a frequency ratio of 35 to 34 is used. Of course any other favorable frequency ratio can be chosen. In case of the first magnetic drive field the currents flowing through the drive field coils 136a, 136b, 136c for example may have the following frequencies: $f_x=f_1$ for the x-coil pair and $$f_y = \frac{35}{34} \cdot f_1$$

for the y-coil pair. This results in a 2D periodic Lissajous figure in the x-y-plane. Of course appropriate 2D Lissajous figures in any other plane may be generated by appropriate currents flowing through the drive field coils. Advantageously the 2D Liassajous figure existing in the x-y-plane is moved in z-direction by creating an appropriate magnetic focus field, resulting in a 3D trajectory.

In case of the second magnetic drive field the currents flowing through the drive field coils 136a, 136b, 136c for example may have the following frequencies: $f_x=f_2$ for the x-coil pair and $$f_y = \frac{35}{34} \cdot f_2$$

for the y-coil pair. This results in a 2D periodic Lissajous figure in the x-y-plane. The further abovementioned explanations concerning the first magnetic drive field are accordingly valid for the second magnetic drive field.

The first and second drive field frequencies $f_1$ and $f_2$ are chosen according to the frequency conditions $f_1 < 100$ kHz and 1 MHz $< f_2 < 10$ MHz. The fact that for both magnetic drive fields the same frequency ratio is chosen shall not have any restricting impact on the invention. Of course different frequency ratios for the first magnetic drive field and the second magnetic drive field may be chosen. Using the same frequency ratio has the advantage that the two sub-zones 52, 54 and therefore the FFP take up the same positions in space along a first trajectory corresponding to the first drive field frequency and along a second trajectory corresponding to the second drive field frequency. For this purpose the 2D Lissajous figure existing in the x-y-plane is advantageously moved similar in z-direction for both magnetic drive fields.

In a step 184 a first particle distribution quantity C1($r$) depending on the first set of detection signals and a second particle distribution quantity C2($r$) depending on the second set of detection signals are reconstructed. The first particle distribution quantity $C_1(r)$ corresponds to the first drive field frequency $f_1$, which is a low frequency, at which field distortion effects due to object properties are negligible. Therefore, the first particle distribution quantity $C_1(r)$ solely represents the distribution of the magnetic particles. The second particle distribution quantity $C_2(r)$ corresponds to the second drive field frequency $f_2$, which is a high frequency, at which field distortion effects occur. Therefore, the second particle distribution quantity $C_2(r)$ represents the distribution of the magnetic particles blurred by the field distortion effects.

The difference between the two measurements conducted at two different drive field frequencies $f_1$ and $f_2$ and therefore the difference between the two particle distribution quantities $C_1(r)$ and $C_2(r)$ can be taken as a contrast itself. However, it does not reflect the patient's electric properties directly. Instead, this contrast can be used to deduce the spatial magnetic field distribution throughout a body, in particular a patient via performing measurements with different frequencies.

In a step 186 an actual magnetic field strength quantity is determined. For this purpose the following approach is chosen: The first particle distribution quantity $C_1(r)$, measured at the first drive field frequency $f_1$ and showing no field distortion effects and the second particle distribution quantity $C_2(r)$, measured at the second drive field frequency $f_2$ and showing filed distortion effects due to the conductivity and/or permittivity influence, can be used for calculating a ratio of coil sensitivities $S_1(r)$ and $S_2(r)$ at different frequencies, wherein both sensitivities primarily represent the sensitivity of the receiving coils and additionally in a certain extent the sensitivity of the drive field coils:

$$\frac{C_1(r)}{C_2(r)} = \frac{S_1(r)}{S_2(r)}. \tag{1}$$

According to the following equation the sensitivities $S_1(r)$ and $S_2(r)$ can be calculated from the magnetic field H using a constant normalizing factor "a":

$$S(r) = \alpha \cdot H \tag{2}$$

This gives a direct relation between the reconstructed particle distribution quantity and the magnetic field:

$$\frac{C_1(r)}{C_2(r)} = \frac{H_1(r)}{H_2(r)}. \tag{3}$$

Equation (3) holds for all Cartesian components of H, depending on the coil and particularly the coil orientation chosen.

Based on equation (3) the following equation can be derived:

$$H_2(r) = \frac{C_2(r)}{C_1(r)} \cdot H_1(r). \tag{4}$$

$H_1(r)$ represents the magnetic field at the first drive field frequency $f_1$ and therefore at a low frequency. Hence $H_1(r)$ can easily be derived from the coil geometry using Biot-Savarts law. The geometry and electric properties of the body to be examined, in particular a patient, are not required for this calculation. $H_2(r)$ is the resulting map to be used for the electric properties calculation. According to equation (4) the actual magnetic field strength quantity $H_2(r)$ is determined depending on the first and the second particle distribution quantity $C_1(r)$, $C_2(r)$ and depending on a reference magnetic field strength quantity $H_1(r)$. This approach is based on the fact, that the distribution of the contrast agent and therefore the distribution of the magnetic particles present within the object to be examined are invariant for the two measurements at different frequencies. In other words: said distributions do not vary with the drive field frequency, the magnetic particles are stationary. Advantageously the reference magnetic field strength quantity $H_1(r)$ is determined by the manufacturer of the MPI apparatus and is stored in the storage unit 162.

In a step 190 the electromagnetic quantity is determined.

As the $H_{x2}(r)$ component is dominant the other two Cartesian components $H_{y2}(r)$ and $H_{z2}(r)$ are negligible. $H_{x2}(r)$ is dominant because of the dominant x-direction component of the magnetic drive field. Based on the actual magnetic field strength quantity $H_{x2}(r)$ determined using equation (4) a conductivity quantity $\epsilon(r)$ characterizing a conductivity distribution throughout the portion of the object to be examined and/or a permittivity quantity $\sigma(r)$ characterizing a permittivity distribution throughout the portion of the object to be examined can for example be determined according to Electromagnetic Properties Tomography via the following equation corresponding to the drive field:

$$\frac{\oint_{\partial A_{yz}} \{-\partial_z H_{x2}(r), \partial_y H_{x2}(r)\} \cdot dl}{\mu \omega^2 \int_{A_{yz}} H_{x2}(r) dy dz} = \frac{\oint_{\partial A_{yz}} \kappa(r) E(r) \cdot dl}{\oint_{\partial A_{yz}} E(r) \cdot dl} \tag{5}$$

$$\approx \kappa(r)$$

$$\equiv \varepsilon(r) - i\sigma(r)/\omega.$$

The quantities contained in equation (5) have the following meaning:

$A_{yz}$: infinitesimal integration area perpendicular to $H_{x2}$.
dl: infinitesimal section of the curve along which the line integral is evaluated.
µ: permeability of the examined object.
ω: angular frequency, $\omega = 2\pi f_2$.
κ(r): complex permittivity.
ε(r): scalar permittivity, being the real part of the complex permittivity.
σ(r): scalar electrical conductivity, being proportional to the imaginary part of the complex permittivity.
E(r): electric field strength.
r: vector in space, representing the x-, y- and z-coordinates of a point in space.
i: imaginary unit.

The scalar electrical conductivity σ(r) is the conductivity quantity to be determined with the apparatus according to the invention and the corresponding method. The scalar permittivity ε(r) is the permittivity quantity to be determined with the apparatus according to the invention and the corresponding method. Both quantities can be derived from complex permittivity κ(r) using well known measures for extracting the real part and the imaginary part of a complex number. The complex permittivity κ(r) is the result of solving equation (5) using well known measures for solving such equations.

Equation (5) is derived from Faraday's law in integral form given by $$-i\omega\mu \int_A H(r)da = \oint_{\partial A} E(r)dr \qquad (6)$$

and from Ampere's law in differential form written as $$\nabla \times H(r)/i\omega = \epsilon(r)E(r), \qquad (7)$$

both equations belonging to the Maxwell equations. In both equations the quantities H(r), E(r) and ε(r) are complex quantities. Equation (5) is obtained by integrating equation (7) along ∂A and by dividing the integrated version of equation (7) by equation (6).

In a step 192 the electromagnetic quantity determined in step 190 is displayed on the monitor 156. In case a further real measurement shall be conducted step 182 is executed again subsequently to step 192. This option is indicated by a dashed arrow.

Further, it is possible to determine a specific absorption rate quantity SAR in step 190. Said specific absorption rate quantity SAR characterizes a local specific energy absorption rate throughout the portion of an object. In this case a step 188 is executed for determining an electric field strength quantity E(r). Said electric field strength quantity E(r) is for example obtained from dividing equation (7) by equation (5).

The specific absorption rate quantity SAR is obtained from the following equation:

$$SAR_{local} = \int_V \sigma(r)E(r)E^*(r)dv, \qquad (8)$$

with σ(r) obtained from equation (5) and E(r) determined in step 188. As the electric field strength quantity E(r) only has to be determined in case the specific absorption rate quantity SAR is determined, step 188 is presented as an option in FIG. 5, using dashed lines.

Advantageously the control unit 150 is adapted for controlling the drive field signal generator unit 130 for varying the direction of the magnetic drive field. Therefore, the direction of $H_x$ can easily be changed with regard to the object to be examined. This offers the possibility of getting information about the tensor structure of the complex permittivity κ(r). The cancellation of the electric field E(r) in equation (5) is only fulfilled in case κ(r) is isotropic. In case κ(r) is anisotropic, the result of equation (5) depends on the direction of $H_x$. Thus, a variation of the direction of $H_x$ allows an estimation of the anisotropy of κ(r).

The method according to the invention is implemented on a standard MPI apparatus or standard MPI scanner. Said method works independently from the standard MPI contrast mechanisms and adds additional information for diagnosis and therapy monitoring.

With the MPI apparatus or MPI scanner in the first sub-zone 52 the magnetization of the magnetic particles is not saturated. In the second sub-zone 54 the magnetization of the magnetic particles is saturated.

The presentation chosen in FIG. 5, according to which in a first step 182 both sets of detection signals are acquired and according to which in a second step 184 both particle distribution quantities are reconstructed shall not have any restricting impact on the invention. Of course it is possible to acquire the first set of detection signals and to reconstruct the first particle distribution signal in a first step and to acquire the second set of detection signals and to reconstruct the second particle distribution signal in a subsequent second step.

According to the embodiments of the apparatus and the corresponding method for determining an electromagnetic quantity described above the determination of the electromagnetic quantity is based on a generation of two magnetic drive fields showing different drive field frequencies. This shall not have any restricting impact on the invention. Of course, the determination of the electromagnetic quantity can also be based on a generation of two superimposed magnetic fields. A first superimposed magnetic field consists of a first magnetic drive field and a first magnetic focus filed, both showing a first frequency. A second superimposed magnetic field consists of a second magnetic drive field and a second magnetic focus field, both showing a second frequency. It is thinkable that the first magnetic drive field has a dominating drive field component and therefore a first direction allowing measurement in this direction and that the first focus field has a dominating focus field component and therefore a second direction allowing measurement in this direction. The same may apply to the second magnetic drive field and the second magnetic focus field.

There are multiple ways to reconstruct the permittivity quantity from the determined magnetic field. Thus, equation (5) is given as one example how to re-arrange the Maxwell equations to obtain a formula for the permittivity quantity as a function of the magnetic field.

At this point the approach for determining an electromagnetic quantity using a MPI apparatus or scanner shall be described in summary.

For determining an electromagnetic quantity a real spatial distribution of the magnetic particles within the object for which the electromagnetic quantity shall be determined must be known. Further a disturbed spatial distribution of the magnetic particles within said object must be known, too. Based on the difference between both spatial distributions information about the electromagnetic properties of the object can be gathered. The real spatial distribution is that spatial distribution at which no field distortion effects due to objects properties are present or at least these effects are negligible. In contrast, the disturbed spatial distribution is a spatial distribution being influenced by said field distortion effects.

The real spatial distribution as well as the disturbed spatial distribution shall be acquired using a MPI apparatus or MPI scanner. The real spatial distribution must be acquired at low drive field frequencies. The disturbed spatial distribution must be acquired at high drive field frequencies. Alternatively the disturbed spatial distribution might be achieved by simulation.

As both spatial distributions shall be acquired with a MPI apparatus a certain sequence for operating the MPI apparatus is needed, wherein said sequence defines the currents flowing through the selection field coils and/or drive field coils and/or focus filed coils. The sequence has to encode the field of interest more than once. Further, the sequence has to fulfil certain requirements arising from a demanded resolution with which the object of interest must be scanned.

There are several suitable sequences thinkable. At a first sequence a first magnetic drive field showing a first drive field frequency and a second magnetic drive field showing a second drive field frequency are generated successively, wherein both drive field frequencies differ from each other. Particularly, the first drive field frequency shall be a low frequency and the second drive frequency shall be a high frequency. The first sequence consists of two sub-sequences differing in frequency, whereas apart from that both sub-sequences are essentially identical.

At a second sequence a third magnetic drive field is generated, wherein the third magnetic drive field simultaneously shows the first drive field frequency (low frequency) and the second drive frequency (high frequency).

At a third sequence the FFP is moved in one direction along a one-dimensional trajectory, wherein the one-dimensional trajectory is generated by a sinusoidal magnetic drive field. The amplitude of the oscillation describing the movement of the FFP shall be larger than a single voxel contained in the field of interest. The field of interest is divided into a plurality of voxels, wherein the data needed for acquiring the spatial distribution of the magnetic particles within the filed of interest is acquired by scanning each single voxel and by assembling the data obtained for each single voxel. Regarding the voxel being arranged in the centre of the field of interest, the FFP crosses this voxel with maximum velocity. As a result, high frequencies arise. In contrast, for a voxel being arranged at the edge of the field of interest, the FFP crosses such a voxel with a velocity being relatively low. As a result, low frequencies arise. Therefore, with generating a magnetic drive field showing solely one single drive field frequency reconstruction of a voxel at different frequencies is possible. For meeting the requirement of encoding a voxel at different frequencies, the one-dimensional trajectory has to be moved, so that for example the voxel being arranged in the centre of the field of interest is crossed by the FFP at maximum speed one time and at relatively low speed the other time. Moving the one-dimensional trajectory is achieved by generating an appropriate magnetic focus filed.

By applying one of the sequences described above, data can be acquired needed for determining the real spatial distribution and the disturbed spatial distribution. For determining the real spatial distribution a first portion of the acquired data is used, wherein the first portion comprises that data corresponding to low drive field frequencies. Therefore, the real spatial distribution consists of low frequency components. For determining the disturbed spatial distribution a second portion of the acquired data is used, wherein the second portion comprises that data corresponding to high drive field frequencies. Therefore, the disturbed spatial distribution consists of high frequency components. Summarized, for acquiring the real spatial distribution and for acquiring the disturbed spatial distribution roughly half of the acquired data is used in each case.

For conducting electromagnetic quantity anisotropic investigations the sequence should be designed such, that the magnetization of the magnetic particles contained in the object of interest is changed referring to different directions. Advantageously the set of data acquired for the real spatial distribution as well as the set of data acquired for the disturbed spatial distribution shall contain for the majority of voxels contained in the field of interest data referring to at least two different directions. Ideally both sets of data contain data referring to all three directions.

By additionally modelling the influence on the magnetic drive field caused by the change of the magnetization of the magnetic particles the results can be improved.

The real spatial distribution and the disturbed spatial distribution and therefore the electromagnetic quantity are reconstructed by solving the following equation $$|\text{vec}\{M_{expected}\} - \text{vec}\{M_{measured}\}\| = ^!\min, \quad (9)$$

that means a norm, for example an Euclidian norm has to be minimized. $M_{measured}$ represents measured data contained in the detection signals acquired with the receiving means. $M_{expected}$ represents calculated data, wherein the calculated data represent those measured data being expected based on theoretical reflections. The Term vec{ } stands for a vector. For the real spatial distribution as well as for the disturbed spatial distribution equation (9) has to be solved.

$M_{expected}$ can be calculated on basis of $$\text{vec}\{M_{expected}\} = f_{receiver}(\text{vec}\{A\}, \text{vec}\{G\}, \text{vec}\{H\}) \quad (10)$$

this can be done using a Maxwell-Solver and a forward pass based on vec{G}.

vec{G} is a model of the magnetic response of the magnetic particles depending on the applied magnetic fields also referred to as system function. In case the distortion of magnetic drive field shall be considered vec{G} has to determined for a set of distorted magnetic drive fields for example by applying of a suitable interpolation.

vec{A} is a model characterizing the MPI scanner and the object of interest. vec{A} contains therefore a set of MPI scanner parameters and a set of object parameters. MPI scanner parameters are for example the position of the coils, the number of coils or windings, quantities characterizing the behaviour or properties of the magnetic material, etc. Object parameters are for example the spatial distribution of the magnetic particles vec{C}, the electrical conductivity vec{σ} also referred to as σ(r) showing anisotropic behaviour and eventually a dependence on the frequency of the electrical conductivity in parametric formulation.

vec{H} represents the resulting magnetic field within the object of interest, in fact with regard to the three direction in space (x, y, z) and for an arbitrary time step and for an arbitrary position within the object of interest.

vec{H} can be determined using the following equation $$\text{vec}\{H\} = f_{transmit}(\text{vec}\{A\}, \text{vec}\{S\}) \quad (11)$$

Vec{S} represents the sequence that is the succession of the currents flowing through the selection field coils and/or the drive field coils and/or the focus field coils.

$F_{transmit}$ is a function mapping the sequence vec{S} on the magnetic field within the object of interest. Therefore, $F_{transmit}$ is a Maxwell-Solver. $F_{transmit}$ receives the MPI scanner geometry and the conductivity of the object of interest as input variables.

Equation (9) is solved by varying vec{A}, that means by varying the conductivity of the object of interest and the spatial distribution of the magnetic particles. This is done by applying one of the common iterative algorithms or methods, as for example conjugated gradient or ART or simulated annealing, etc. The MPI scanner parameters are not or solely slightly varied, because they are determined in advance by conducting calibration measurements.

The apparatus and the corresponding method as described above, as well as the related computer program may not only be applied to medical areas. They might also be applied to non-medical areas, e.g. contact-less material testing, as long as the material to be tested is suitable for MPI.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit

The invention claimed is:

1. An apparatus (100) for determining at least one electromagnetic quantity characterizing an electromagnetic property of an object, wherein said object contains magnetic particles, which apparatus comprises:
   selection means comprising a selection field signal generator unit (110) and selection field elements (116) for generating a magnetic selection field (50) having a pattern in space of a magnetic field strength such that a first sub-zone (52) having a low magnetic field strength and a second sub-zone (54) having a higher magnetic field strength are formed in a field of view (28);
   drive means comprising a drive field signal generator unit (130) and drive field coils (136a, 136b, 136c) for changing the position in space of the two sub-zones (52, 54) in the field of view (28) by means of a magnetic drive field so that a magnetization of the magnetic particles contained in said object changes locally;
   receiving means comprising at least one signal receiving unit (140) and at least one receiving coil (148) for acquiring detection signals, which detection signals depend on the magnetization in the field of view (28), which magnetization is influenced by the change in the position in space of the first and second sub-zone (52, 54);
   a reconstruction unit (152) for reconstructing a particle distribution quantity characterizing a spatial distribution of the magnetic particles within at least a portion of the object depending on the detection signals; and
   a control unit (150) for controlling the receiving unit for acquiring a first set of detection signals corresponding to a first drive field frequency and for acquiring a second set of detection signals corresponding to a second drive field frequency, wherein the first and the second drive field frequency differ from each other, and for controlling the reconstruction unit (152) for reconstructing a first particle distribution quantity depending on the first set of detection signals and for reconstructing a second particle distribution quantity depending on the second set of detection signals, wherein the reconstruction unit (152) contains a determination unit (160) for determining the electromagnetic quantity as a function of different distortion effects by the first and the second particle distribution quantity.

2. An apparatus (100) as claimed in claim 1, wherein the control unit (150) is adapted for controlling the drive field signal generator unit (130) for generating a first magnetic drive field showing the first drive field frequency and for generating a second magnetic drive field showing the second drive field frequency.

3. An apparatus (100) as claimed in claim 2, wherein the control unit (150) is adapted for controlling the drive field signal generator unit (130) so that the first and the second magnetic drive field are generated successively.

4. An apparatus (100) as claimed in claim 2, wherein the two sub-zones (52,54) take up first positions in space along a first trajectory corresponding to the first drive field frequency and second positions in space along a second trajectory corresponding to the second drive field frequency, wherein the control unit (150) is adapted for controlling the drive field signal generator unit (130) so that the first positions and the second positions substantially correspond to each other.

5. An apparatus (100) as claimed in claim 1, wherein the control unit (150) is adapted for controlling the drive field signal generator unit (130) for generating a third magnetic drive field showing simultaneously the first and the second drive field frequency.

6. An apparatus (100) as claimed in claim 1, wherein the determination unit (160) is adapted for determining the electromagnetic quantity depending on a quotient formed with the first and the second particle distribution quantity.

7. An apparatus (100) as claimed in claim 1, wherein the determination unit (160) is adapted for determining an actual magnetic field strength quantity depending on the first and the second particle distribution quantity for determining the electromagnetic quantity.

8. An apparatus (100) as claimed in claim 7, wherein the determination (160) is adapted for determining the actual magnetic field strength quantity depending on a reference magnetic field strength quantity.

9. An apparatus (100) as claimed in claim 1, wherein the control unit (150) is adapted for controlling the drive field signal generator unit (130) for varying the direction of the magnetic drive field.

10. An apparatus (100) as claimed in claim 1, wherein the apparatus further comprises a storage unit (162) for storing a set of system data of the apparatus' system function.

11. apparatus (100) as claimed in claim 1, wherein the determination unit (160) is adapted fir determining an electric field strength quantity.

12. An apparatus (100) as claimed in claim 1, wherein as electromagnetic quantity at least one of a conductivity quantity characterizing a conductivity distribution throughout the portion of the object, a permittivity quantity characterizing a permittivity distribution throughout the portion of the object and a specific absorption rate quantity characterizing a local specific energy absorption rate throughout the portion of the object is determined.

13. An apparatus (100) as claimed in claim 1, wherein the reconstruction unit (152) is adapted fir transmitting the electromagnetic quantity to a computer (154) for displaying the spatial distribution of the electromagnetic quantity throughout the portion of the object on a monitor (156).

14. A method for determining at least one electromagnetic quantity characterizing an electromagnetic property of an object, wherein said object contains magnetic particles, which method comprises the steps of:
   generating a magnetic selection field (50) having a pattern in space of a magnetic field strength such that a first sub-zone (52) having a low magnetic field strength and a second sub-zone (54) having a higher magnetic field strength are formed in a field of view (28);
   changing the position in space of the two sub-zones (52, 54) in the field of view (28) by means of a magnetic drive field so that a magnetization of the magnetic particles contained in said object changes locally;
   acquiring detection signals, which detection signals depend on the magnetization in the field of view (28), which magnetization is influenced by the change in the position in space of the first and second sub-zone (52, 54);
   reconstructing a particle distribution quantity characterizing a spatial distribution of the magnetic particles within at least a portion of the object depending on the detection signals;
   controlling the acquiring of a first set of detection signals corresponding to a first drive field frequency and the acquiring of a second set of detection signals corresponding to a second drive field frequency, wherein the first and the second drive field frequency differ from each other;

controlling the reconstructing of a first particle distribution quantity depending on the first set of detection signals and the reconstructing of a second particle distribution quantity depending on the second set of detection signals; and determining the electromagnetic quantity as a function of different distortion effects by the first and the second particle distribution quantity.

15. A non-transitory computer program comprising program code means for determining at least one electromagnetic quantity characterizing an electromagnetic property of an object, wherein said object contains magnetic particles, wherein the computer program comprises program code for causing a computer to carry out the following steps when the computer program is run on the computer:

generating a magnetic selection field (50) having a pattern in space of a magnetic field strength such that a first sub-zone (52) having a low magnetic field strength and a second sub-zone (54) having a higher magnetic field strength are formed in a field of view (28);

changing the position in space of the two sub-zones (52, 54) in the field of view (28) by means of a magnetic drive field so that a magnetization of the magnetic particles contained in said object changes locally;

acquiring detection signals, which detection signals depend on the magnetization in the field of view (28), which magnetization is influenced by the change in the position in space of the first and second sub-zone (52, 54);

reconstructing a particle distribution quantity characterizing a spatial distribution of the magnetic particles within at least a portion of the object depending on the detection signals;

controlling the acquiring of a first set of detection signals corresponding to a first drive field frequency and the acquiring of a second set of detection signals corresponding to a second drive field frequency, wherein the first and the second drive field frequency differ from each other;

controlling the reconstructing of a first particle distribution quantity depending on the first set of detection signals and the reconstructing of a second particle distribution quantity depending on the second set of detection signals; and determining the electromagnetic quantity as a function of different distortion effects by the first and the second particle distribution quantity.

* * * * *